(12) United States Patent
Prew et al.

(10) Patent No.: US 9,511,239 B2
(45) Date of Patent: Dec. 6, 2016

(54) ELECTRODE WITH FEATURE FOR INDICATING PRIOR USE WITH ADULT OR PEDIATRIC SUBJECT AND SYSTEMS AND METHODS INCLUDING SAME

(71) Applicant: ZOLL MEDICAL CORPORATION, Chelmsford, MA (US)

(72) Inventors: Paul F. Prew, Attleboro, MA (US); Deborah T. Jones, Dartmouth, MA (US); David N. Craige, III, Attleboro, MA (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 54 days.

(21) Appl. No.: 14/494,212

(22) Filed: Sep. 23, 2014

(65) Prior Publication Data
US 2015/0094782 A1     Apr. 2, 2015

Related U.S. Application Data

(60) Provisional application No. 61/883,239, filed on Sep. 27, 2013.

(51) Int. Cl.
| | | |
|---|---|---|
| *A61N 1/04* | (2006.01) | |
| *A61N 1/08* | (2006.01) | |
| *A61N 1/39* | (2006.01) | |

(52) U.S. Cl.
CPC ............. *A61N 1/3937* (2013.01); *A61N 1/046* (2013.01)

(58) Field of Classification Search
CPC ........ A61N 1/04; A61N 1/046; A61N 1/0484; A61N 1/0492; A61N 1/36014; A61N 1/3625; A61N 1/38; A61N 1/3937; A61N 1/3993

USPC .................................................. 607/5, 7, 142
See application file for complete search history.

(56) References Cited

U.S. PATENT DOCUMENTS

| | | |
|---|---|---|
| 5,243,978 A | 9/1993 | Duffin, Jr. |
| 6,141,584 A | 10/2000 | Rockwell et al. |
| 6,148,233 A | 11/2000 | Owen et al. |
| 6,356,785 B1 | 3/2002 | Snyder et al. |
| 6,405,083 B1 | 6/2002 | Rockwell et al. |
| 6,438,417 B1 | 8/2002 | Rockwell et al. |
| 6,597,948 B1 | 7/2003 | Rockwell et al. |
| 6,920,354 B2 | 7/2005 | Daynes et al. |
| 7,231,258 B2 | 6/2007 | Moore et al. |
| 7,769,465 B2 | 8/2010 | Matos |
| 2001/0047140 A1 | 11/2001 | Freeman |

(Continued)

FOREIGN PATENT DOCUMENTS

DE           3110915 A1    12/1982

OTHER PUBLICATIONS

Aramendi et al. "A Simple Effective Filtering Method for Removing CPR Caused Artefacts from Surface ECG Signals". Computers in Cardiology. Sep. 25, 2005.

(Continued)

*Primary Examiner* — Allen Porter, Jr.
(74) *Attorney, Agent, or Firm* — The Webb Law Firm (57) ABSTRACT

Methods and systems of applying treatment to a subject experiencing cardiac distress. In one example, there is provided a defibrillation electrode. The defibrillation electrode includes a non-volatile memory element and a circuit configured to store an indication of a level of energy delivered to a subject during the application of a defibrillation shock to the subject in the non-volatile memory element.

25 Claims, 6 Drawing Sheets

(56) References Cited

U.S. PATENT DOCUMENTS

| | | | |
|---|---|---|---|
| 2004/0143298 A1 | 7/2004 | Nova et al. | |
| 2004/0210170 A1 | 10/2004 | Palazzolo et al. | |
| 2004/0249419 A1* | 12/2004 | Chapman | A61N 1/3925 607/5 |
| 2006/0015044 A1 | 1/2006 | Stavland et al. | |
| 2007/0196320 A1 | 8/2007 | Yasin | |
| 2007/0197926 A1 | 8/2007 | Danehorn et al. | |
| 2007/0233199 A1 | 10/2007 | Moore et al. | |
| 2007/0299473 A1 | 12/2007 | Matos | |
| 2008/0004663 A1 | 1/2008 | Jorgenson | |
| 2010/0164612 A1 | 7/2010 | Koyrakh | |
| 2010/0292748 A9 | 11/2010 | Stickney et al. | |
| 2010/0324612 A1 | 12/2010 | Matos | |
| 2011/0034836 A1 | 2/2011 | Halperin et al. | |
| 2011/0105930 A1 | 5/2011 | Thiagarajan et al. | |
| 2011/0288604 A1 | 11/2011 | Kaib et al. | |
| 2012/0146797 A1 | 6/2012 | Oskin et al. | |
| 2014/0277226 A1* | 9/2014 | Poore | A61N 1/3987 607/7 |

OTHER PUBLICATIONS

Association for the Advancement of Medical Instrumentation, ANSI/AAMI DF80:2003 Medical Electrical Equipment—Part 2-4: Particular Requirements for the Safety of Cardiac Defibrillators (including Automated External Defibrillators) 2004, ISBN 1-57020-210-9; abstract; p. vi; p. 50, section 107.1.2.

Romero et al. "Motion Artifact Reduction in Ambulatory ECG Monitoring: An Integrated System Approach". Wireless Health. Oct. 10, 2011.

* cited by examiner

ELECTRODE WITH FEATURE FOR INDICATING PRIOR USE WITH ADULT OR PEDIATRIC SUBJECT AND SYSTEMS AND METHODS INCLUDING SAME

RELATED APPLICATIONS

This application claims priority under 35 U.S.C. §119(e) to U.S. Provisional Application Ser. No. 61/883,239, titled "ELECTRODE WITH FEATURE FOR INDICATING PRIOR USE WITH ADULT OR PEDIATRIC SUBJECT AND SYSTEMS AND METHODS INCLUDING SAME," filed on Sep. 27, 2013, which is herein incorporated by reference in its entirety.

BACKGROUND

1. Technical Field

Aspects and embodiments of the present invention relate to systems and methods for the treatment of individuals experiencing cardiac distress.

2. Discussion of Related Art

Treatment of a subject experiencing cardiac distress can generally include clearing the subject's airway, assisting the subject's breathing, chest compressions, and defibrillation.

Defibrillation can be performed with the use of an automatic external defibrillator (AED). Most automatic external defibrillators are actually semi-automatic external defibrillators (SAED), which require a responder to press a start button, after which the defibrillator analyzes the subject's condition, provides a shock to the subject if the electrical rhythm is shockable, and waits for user intervention before any subsequent shock. Fully automatic external defibrillators, on the other hand, do not wait for user intervention before applying subsequent shocks. As the term is used herein, automatic external defibrillators (AED) include semi-automatic external defibrillators (SAED).

Both types of defibrillators typically provide an oral stand clear warning before the application of each shock, and then the responder is expected to stand clear of the subject and may be required to press a button indicating that the responder is standing clear of the subject. The controls for automatic external defibrillators are typically located on a control panel of the defibrillator.

AEDs are typically used by trained providers such as physicians, nurses, fire department personnel, and police officers. There might be one or two people at a given facility that has an AED who has been trained to provide emergency aid, such as defibrillation and/or CPR before an ambulance service arrives. The availability of on-site AEDs along with rescuers trained to operate them is important because if the subject experiences a delay of more than about 90 seconds before receiving a defibrillation shock, the subject's chance of survival can drop dramatically. Many large cities and rural areas have low survival rates for defibrillation because the ambulance response time is slow. Many suburbs have higher survival rates because of the faster ambulance response time due to lack of traffic and availability of hospitals and advanced life support.

Trained lay providers are a new group of AED operators, but they rarely have opportunities to defibrillate. For example, spouses of heart attack victims may become lay providers, but these lay providers can be easily intimidated by an AED during a medical emergency. Consequently, such lay providers can be reluctant to purchase AEDs, or might tend to wait for an ambulance to arrive rather than use an available AED, out of concern that the lay provider might do something wrong.

SUMMARY

In accordance with a first aspect, there is provided a defibrillation electrode. The defibrillation electrode comprises a non-volatile memory element and at least one of a circuit and software configured to store, in the non-volatile memory element, an indication of a level of energy delivered to a subject during the application of a defibrillation shock to the subject. The defibrillation electrode may include a marking providing an indication of the presence of the non-volatile memory element. The defibrillation electrode may further include an electrical connector configured to releasably electrically couple the defibrillation electrode to a defibrillator.

In some embodiments, at least one of the circuit and software is further configured to query a defibrillator to which the electrode is attached for one or more energy level settings of the defibrillator. In other embodiments, the circuit is further configured to measure an energy level of a defibrillation shock delivered to the subject during application of the defibrillation shock to the subject. In other embodiments, the circuit is further configured to output a signal indicative of the energy level of the defibrillation shock delivered to the subject during the application of the defibrillation shock to the subject responsive to a query from a defibrillator. The indication of the level of energy may be an indication of whether a defibrillator which applied a defibrillation shock through the electrode was set in a pediatric mode or in an adult mode.

In accordance with another aspect, there is provided a defibrillation electrode pad. The defibrillation electrode pad comprises a defibrillation electrode, a non-volatile memory element, and a circuit configured to store, in the non-volatile memory element, an indication of a level of energy delivered to a subject through the defibrillation electrode during the application of a defibrillation shock to the subject.

In accordance with another aspect, there is provided a defibrillation system. The system comprises a defibrillation electrode including a non-volatile memory element and a circuit configured to store, in the non-volatile memory element, an indication of a level of energy delivered to a subject during the application of a defibrillation shock to the subject. The defibrillation electrode may include an electrical connector configured to releasably electrically couple the defibrillation electrode to a defibrillator. The system further comprises a first defibrillator configured to provide a signal to the defibrillation electrode indicative of the level of energy delivered to the subject during the application of the defibrillation shock.

In some embodiments, a defibrillation energy level delivered by the first defibrillator is adjustable. The defibrillation energy delivered by the first defibrillator may be selectable between a pediatric energy level and an adult energy level.

In some embodiments, the system further comprises a second defibrillator configured to electrically couple to the electrode through the electrical connector. The second defibrillator may be configured to read the indication of the level of energy delivered to the subject from the non-volatile memory element. The second defibrillator may be configured to automatically read the indication of the level of energy delivered to the subject from the non-volatile memory element. The second defibrillator may be configured to read the indication of the level of energy delivered to the subject from the non-volatile memory element responsive to a command from a user.

In some embodiments, the second defibrillator is configured to set a defibrillation energy level to a level consistent with an energy level determined from the indication of the level of energy delivered to the subject read from the non-volatile memory element. The second defibrillator may be configured to display the set defibrillation energy level. The second defibrillator may include an override configured to provide for an adjustment of the set defibrillation energy level.

In accordance with another aspect, there is provided a method for treatment of a subject experiencing cardiac distress. The method comprises attaching a pair of electrodes to the subject, electrically coupling the pair of electrodes to a first defibrillator, defibrillating the subject with the first defibrillator, and recording an indication of a defibrillation energy setting of the first defibrillator in a non-volatile memory element included in one of the pair of electrodes. The method may further include decoupling the pair of electrodes from the first defibrillator, electrically coupling the pair of electrodes to a second defibrillator, reading the indication of the defibrillation energy setting of the first defibrillator from the non-volatile memory element into the second defibrillator, and setting a defibrillation energy level of the second defibrillator to a level selected based on the indication of the defibrillation energy setting of the first defibrillator.

In some embodiments, the method further comprises determining the defibrillation energy setting of the first defibrillator, determining if the defibrillation energy setting of the first defibrillator is appropriate for the subject, and adjusting the defibrillation energy setting of the first defibrillator responsive to a determination that the defibrillation energy setting of the first defibrillator is not appropriate for the subject. In some embodiments, the method may further comprise displaying the defibrillation energy level selected by the second defibrillator in a display of the second defibrillator, and in some embodiments, the method may further comprise determining if the defibrillation energy level selected by the second defibrillator is appropriate for the subject, and adjusting a defibrillation energy setting of the second defibrillator responsive to a determination that the defibrillation energy setting of the second defibrillator is not appropriate for the subject.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Aspects and embodiments of the present invention are not limited to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," "having," "containing," "involving," and variations thereof herein is meant to encompass the items listed thereafter and equivalents thereof.

Aspects and embodiments of the present invention include systems and methods which can prevent delivery of an inappropriate level of defibrillation energy to a subject during a defibrillation event. Systems disclosed herein may include electrodes having an indicator which may be read by a defibrillator to determine a level of defibrillation energy previously applied through the electrode to a subject to whom the electrode is attached. The defibrillator may read the indicator and set a power level of defibrillation pulses which may be applied to a subject to a level equal or similar to the power level of defibrillation pulses previously applied through the electrode.

In some situations, defibrillation may be performed on a subject by a first responder or ambulance medic using, for example, an AED or a portable defibrillator electrically coupled to a set of electrodes. The subject may subsequently be moved to a different setting, for example, a hospital. The set of electrodes may remain attached to the subject and connected to a second defibrillation system in an ambulance and/or in the hospital. Systems and methods as disclosed herein may allow for the subject to be provided with a similar level of defibrillation energy from the second defibrillation system as was previously applied by the AED or portable defibrillator. This may be particularly important in the case of pediatric subjects who are typically provided with lower power defibrillation pulses than adult subjects. Aspects and embodiments disclosed herein may provide for a pediatric subject who is shocked with a first defibrillation pulse at an appropriate level from a first defibrillator to receive additional defibrillation pulses from a second defibrillator at an appropriate level, rather than inadvertently being shocked with defibrillation pulses having energy levels more appropriate for adult subjects.

Pediatric and adult subjects requiring defibrillation to correct a shockable abnormal sinus rhythm are typically provided with defibrillation shocks having different energy levels. For example, a pediatric subject may be provided with a series of defibrillation shocks having energy levels of about 50 Joules, about 70 Joules, and about 85 Joules, while an adult subject may be provided with a series of defibrillation shocks having energy levels of about 120 Joules, about 150 Joules, and about 200 Joules. These energy levels may vary from subject to subject depending, for example, on factors such as the age, size, and/or impedance of the subject. Applying defibrillation pulses to a subject having higher energy levels than necessary may result in injury to the subject and thus should be avoided.

Figure 1:
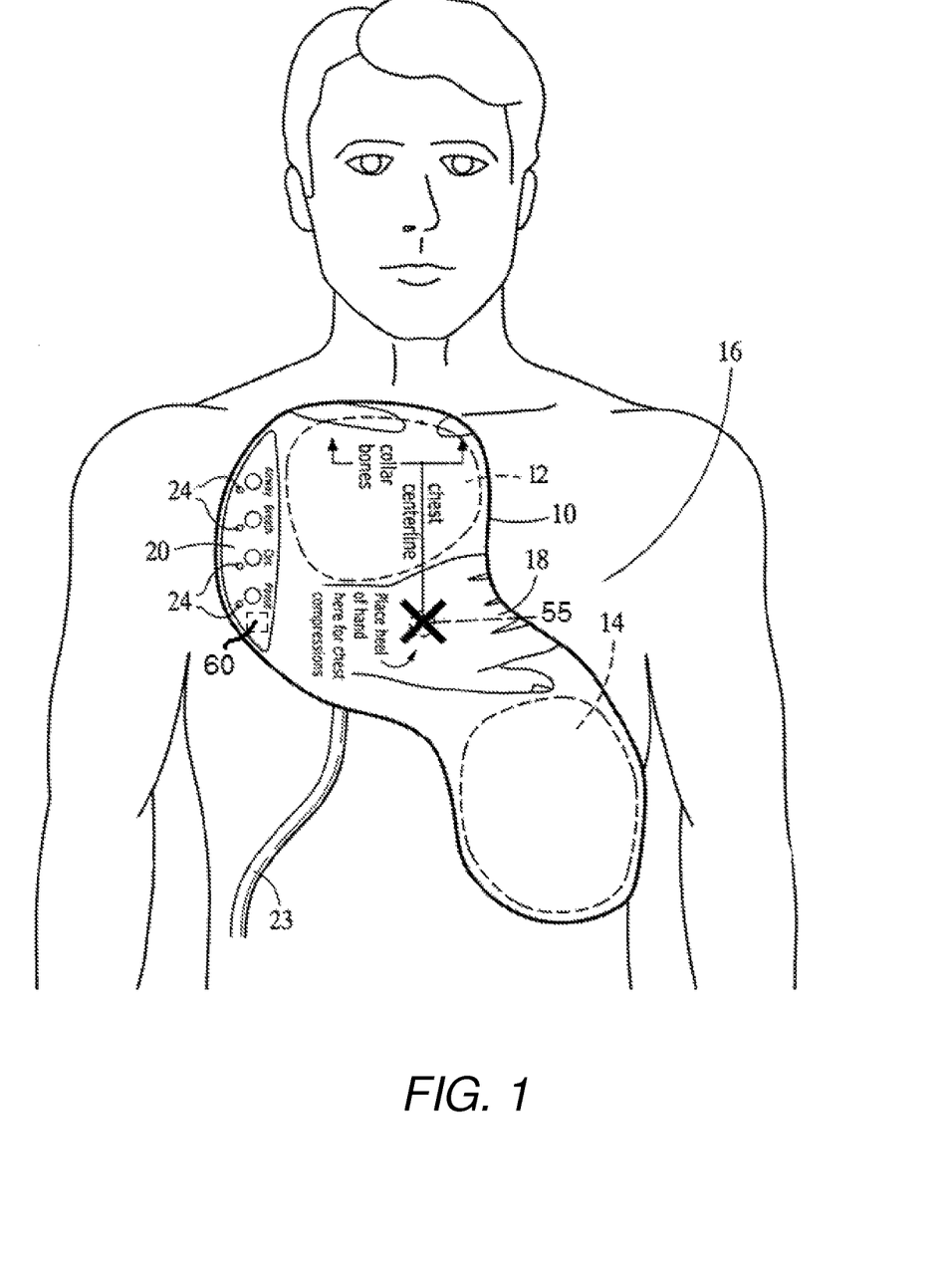
FIG. 1 is a drawing of an embodiment of a defibrillation electrode pad positioned over the chest of a subject.

FIG. 1 illustrates a defibrillation electrode pad 10 similar to those described in commonly owned U.S. patent application Ser. No. 10/954,633, published under Publication No. US20050131465, which is incorporated herein by reference in its entirety. The defibrillation electrode pad 10 includes a high-voltage apex defibrillation electrode 12 and a high-voltage sternum defibrillation electrode 14. In use, the defibrillation electrode pad 10 is placed on a subject's chest 16. The defibrillation electrode pad 10 includes a region 18 on which a user may press to perform CPR. Legends on pad 10 indicate proper placement of the pad with respect to the subject's collarbones and the chest centerline and the proper placement of the heel of the rescuer's hand.

A low-profile button panel 20 is provided on the electrode assembly. Button panel 20 has buttons, including buttons Airway (Airway Help), Breath (Breathing Help), Circ (Circulation Help) and Pause, and may also include adjacent light emitting diodes (LEDs) 24 that indicate which button has been most recently pressed. Button panel 20 is connected by a cable 23 to a remote defibrillator. Button panel 20 provides rigid support underneath buttons Airway, Breath, Circ, and Pause against which the switches can be pushed to ensure good switch closure while the electrode rests on a subject.

A compression or displacement-sensing element 55 such as an accelerometer, for example, a solid-state ADXL202 or ADXL203 accelerometer (available from Analog Devices, Inc. of Norwood, Mass.), is positioned in the defibrillation electrode pad 10 at the location where the rescuer performs chest compressions. The purpose of the displacement-sensing element 55 is to provide an indication to the defibrillator regarding the depth and/or frequency of chest compressions applied during the administration of CPR. The defibrillator may prompt the rescuer to apply additional compression or force or to vary the depth or rate of chest compressions responsive to receipt of a signal from the displacement-sensing element 55 of inappropriate depth and/or frequency of chest compressions being applied.

A memory element 60, for example, an EEPROM or flash memory may be provided in the defibrillation electrode pad 10, for example, in the button panel 20 to record parameters associated with the use of the defibrillation electrode pad 10. These parameters may include, for example, identification information (e.g., model number, date of manufacture, expiration date, etc.) for the defibrillation electrode pad 10 and/or a history of treatment events provided to a subject though the defibrillation electrode pad 10.

Figure 2:
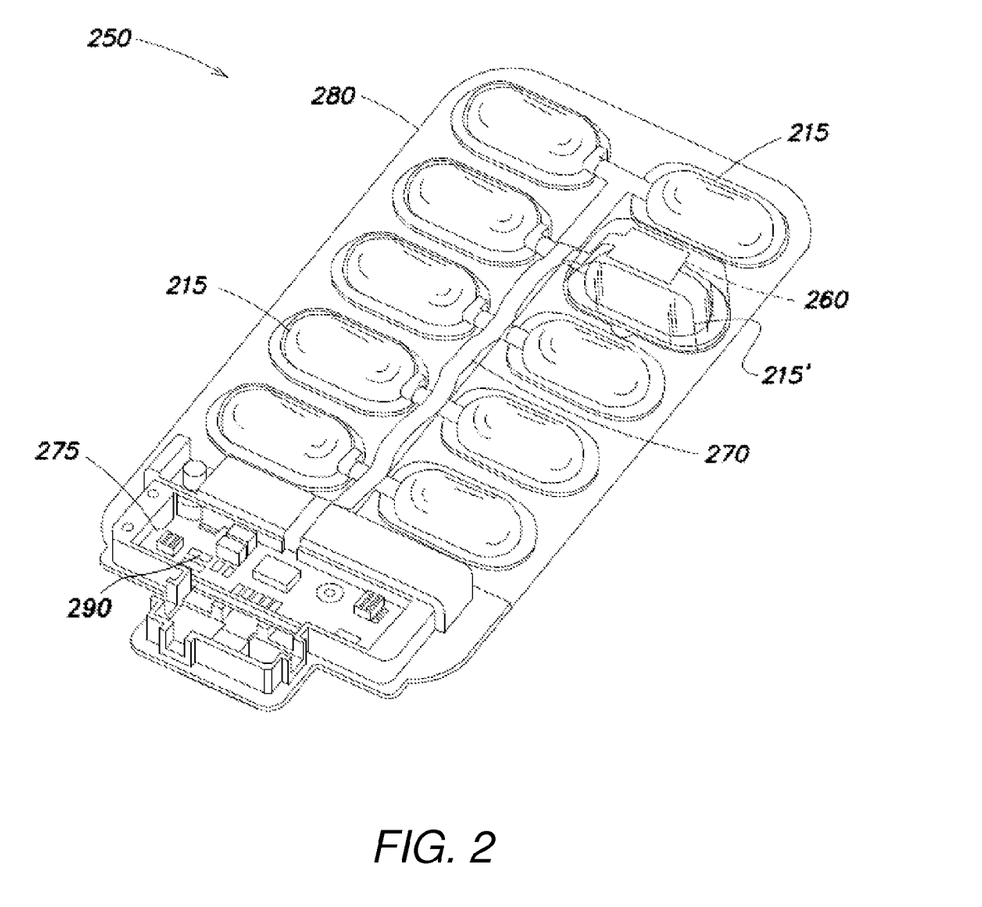
FIG. 2 is an isometric view of an embodiment of a defibrillation electrode.

FIG. 2 illustrates an electrode 250 similar to that described in commonly owned U.S. patent application Ser. No. 14/314,799, which is incorporated herein by reference in its entirety. The electrode 250 includes a substrate 280 upon which is mounted a plurality of conductive gel reservoirs enclosed in caps 215, 215', an acoustic sensor 260, for example, an accelerometer, and a ribbon cable 270 which provides electrical connection between the acoustic sensor 260 and a circuit board 275. The circuit board 275 may incorporate a memory element 290 to record parameters associated with the use of the defibrillation electrode 250. These parameters may include, for example, identification information for the electrode 250 and/or a history of treatment events provided to a subject though the electrode 250 as described with reference to the defibrillation electrode pad 10 illustrated in FIG. 1.

Figure 3A:
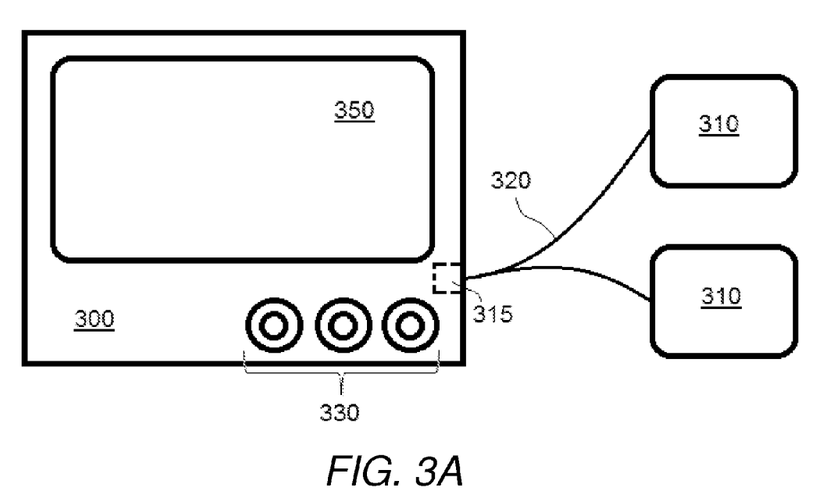
FIG. 3A is a simplified elevational view of an embodiment of a defibrillator.

The electrodes in the defibrillation electrode pad 10 illustrated in FIG. 1 and/or a pair of electrodes 250 as illustrated in FIG. 2 (referred to generally henceforth as electrodes 310) may be applied to a subject in need of defibrillation and electrically coupled to a defibrillator 300 as illustrated in FIG. 3A. It should be understood that the defibrillation electrode pad and electrodes illustrated in FIGS. 1 and 2 are presented only as examples, and aspects and embodiments of the present invention are not limited to electrodes having any particular size, shape, form factor, or components other than those explicitly recited in the claims. In some embodiments, the electrodes 310 may be utilized not only to defibrillate a subject but also to provide one or more additional functions, for example, to monitor an ECG signal from the subject.

The defibrillator 300 may supply energy to provide defibrillation shocks to the subject through the electrodes 310. The electrical coupling of the electrodes 310 to the defibrillator 300 may be though cables 320 which are removably coupled to one or both of the defibrillator 300 and the electrodes 310, for example, through a quick disconnect connector 315. The defibrillator may be an AED provided in a location for use by a first responder or a portable defibrillator, for example, a portable defibrillator provided in an ambulance or other emergency vehicle.

Figure 3B:
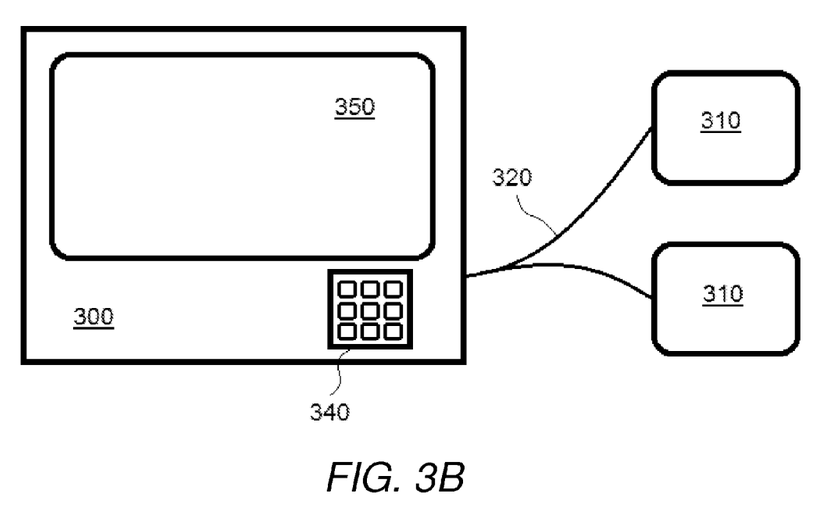
FIG. 3B is a simplified elevational view of an embodiment of a defibrillator.
Figure 3C:
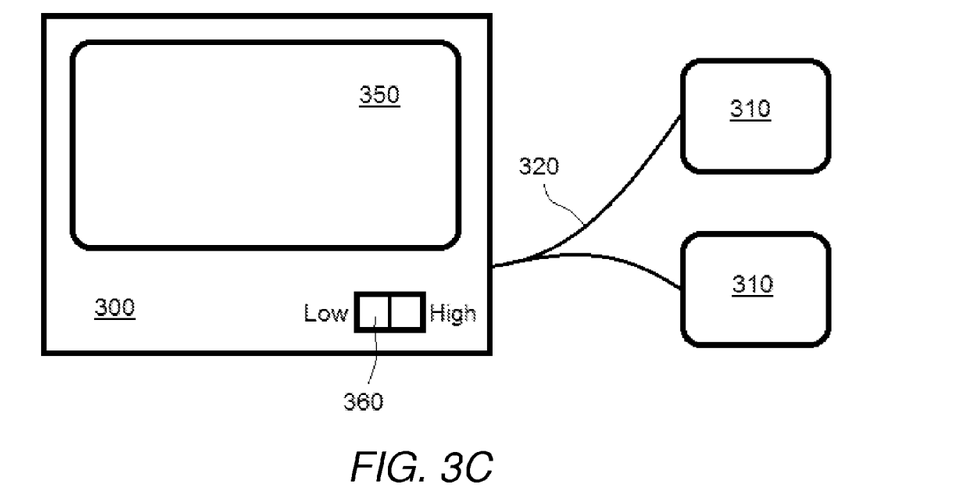
FIG. 3C is a simplified elevational view of an embodiment of a defibrillator.
Figure 3D:
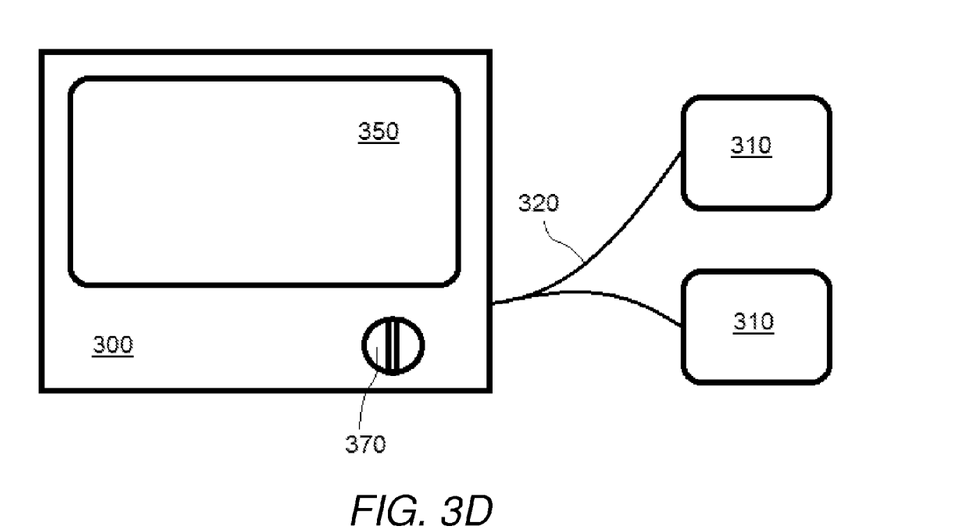
FIG. 3D is a simplified elevational view of an embodiment of a defibrillator.

The defibrillator 300 may include a mechanism for setting the energy level(s) of defibrillation pulses to be supplied. The mechanism for setting the energy level(s) of defibrillation pulses may be configured to provide for a user to select from a variety of different levels. The mechanism for setting the energy level(s) of defibrillation pulses may include, for example, one or more dials 330 (FIG. 3A) or a keypad 340 (FIG. 3B), which may be a mechanical keypad or a virtual keypad provided on a touch screen display 350 of the defibrillator 300. The defibrillator may also or alternatively include a mechanism capable of selecting from a discreet number of different defibrillation power levels, for example from a high (adult) and a low (pediatric) energy level setting. The mechanism may include, for example, a toggle or rocker switch 360 (FIG. 3C). In some embodiments, the switch 360 may be in the form of a key operated switch 370 (FIG. 3D).

At least one of the electrodes 310 includes circuitry, for example, as part of circuit board 275 illustrated in FIG. 2 and/or in circuitry associated with the displacement-sensing element 55 of FIG. 1, which is configured to read the setting(s) of the mechanism for setting the energy level(s) of defibrillation pulses on the defibrillator 300 and to store an indication of this setting or settings in a non-volatile memory element of the electrode, for example, memory element 60 of FIG. 1 or memory element 290 of FIG. 2. Additionally or alternatively, at least one of the electrodes 310 may include circuitry, for example, as part of circuit board 275 illustrated in FIG. 2 and/or in circuitry associated with the displacement-sensing element 55 of FIG. 1, which is configured to measure the energy applied during defibrillation and store an indication of the applied energy in the non-volatile memory element of the electrode.

In some embodiments, at least one of the electrodes 310, or circuitry associated with at least one of the electrodes 310, may provide an indication of whether the applied energy was at a high (adult) or low (pediatric) level. For example, one of the LEDs 24 illustrated in FIG. 1, or an additional LED 24 (not shown) may illuminate responsive to one of a high and a low energy level having been applied to the subject during defibrillation. Additionally or alternatively, the LED 24 may display different colors, blink in different fashions, or otherwise provide an indication of whether a high or a low defibrillation energy level was applied to the subject.

After receiving defibrillation from the defibrillator 300, a subject may be transported to a second location away from the defibrillator 300 and the electrodes 310 may be decoupled from the defibrillator 300 and connected to a second defibrillator. For example, the defibrillator 300 may be an AED which is used to defibrillate a subject who experienced a cardiac event in a location outside a hospital, for example, an office building, residence, or airport. The subject may be transported to a second location other than the one at which the subject experienced the cardiac event, for example, to a hospital. The electrodes 310 may remain adhered to the subject during transport and coupled to a second defibrillator at the hospital. The electrodes 310 may additionally have been connected to an intermediate portable defibrillator during transport of the subject to the second location, for example, in an ambulance.

Figure 4:
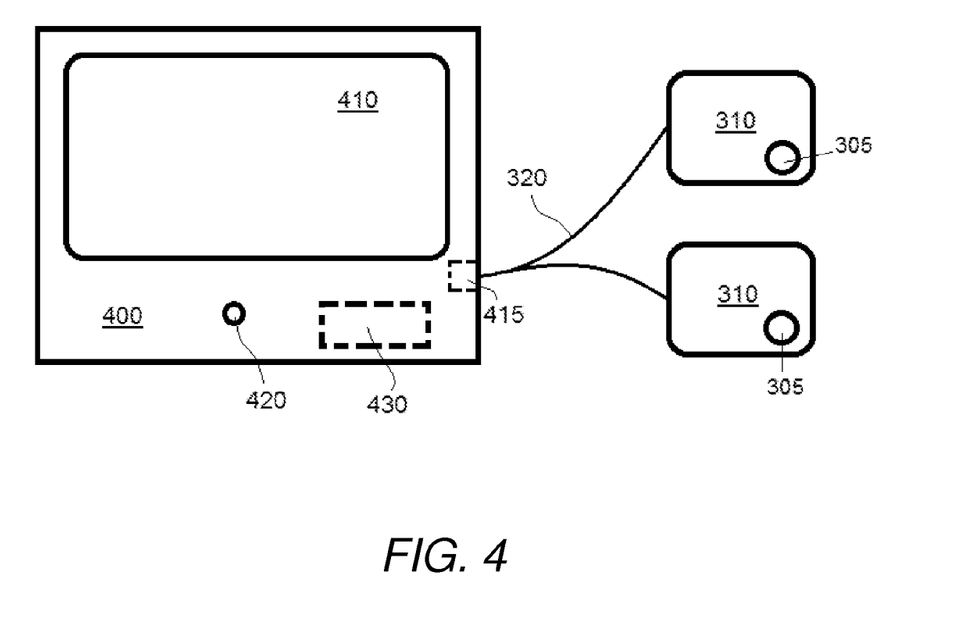
FIG. 4 is a simplified elevational view of an embodiment of a defibrillator.

In some embodiments, the electrodes 310 may be connected, for example, through a quick release connector 415 to the second defibrillator 400 at the second location. The second defibrillator 400 may be configured to read the indication of the defibrillation energy settings from the first defibrillator 300 and/or the indication of the energy applied by the first defibrillator 300 which is stored in the memory element of the electrodes 310. The second defibrillator 400 may be configured to automatically query the electrodes for information pertaining to the defibrillation energy settings from the first defibrillator 300 and/or the indication of the energy applied by the first defibrillator 300. Alternatively, the second defibrillator 400 may be configured query the electrodes for information pertaining to the defibrillation energy settings from the first defibrillator 300 and/or the indication of the energy applied by the first defibrillator 300 responsive to a command from a caregiver. The electrodes 310 may include markings indicating that the electrodes 310 include a memory element which may be read by the second defibrillator 400 to obtain the defibrillation energy settings from the first defibrillator 300 and/or the indication of the energy applied by the first defibrillator 300. These markings may prompt a caregiver to command the second defibrillator 400 to query the electrodes 310 to obtain the power level(s) of the previously applied defibrillation shock(s).

The second defibrillator 400 may set a level or levels of energy to be delivered the subject upon defibrillation, if and when needed, that is consistent with the defibrillation energy level or levels previously applied by the first defibrillator 300. The second defibrillator 400 may include a display 410 which provides a notification that an indication of an energy level of a defibrillation shock previously applied to the subject through the electrodes 310 was detected and read from the memory element of the electrodes 310. The second defibrillator 400 may also display the energy levels read from the memory element of the electrodes 310. In some embodiments, the second defibrillator 400 may include a button 420 or a soft key on the display 410 which allows a caregiver to override the defibrillation energy level or levels set based on the reading of the memory element of the electrodes 310 if the caregiver should determine that different defibrillation energy levels should be used for the subject. The second defibrillator 400 may include a mechanism 430, for example, any one or more of a set of dials, a keypad, toggle switch, or key operated switch similar to those described above with reference to the first defibrillator 300 by which the caregiver may adjust an energy level of a defibrillation shock to be applied to the subject.

Figure 5:
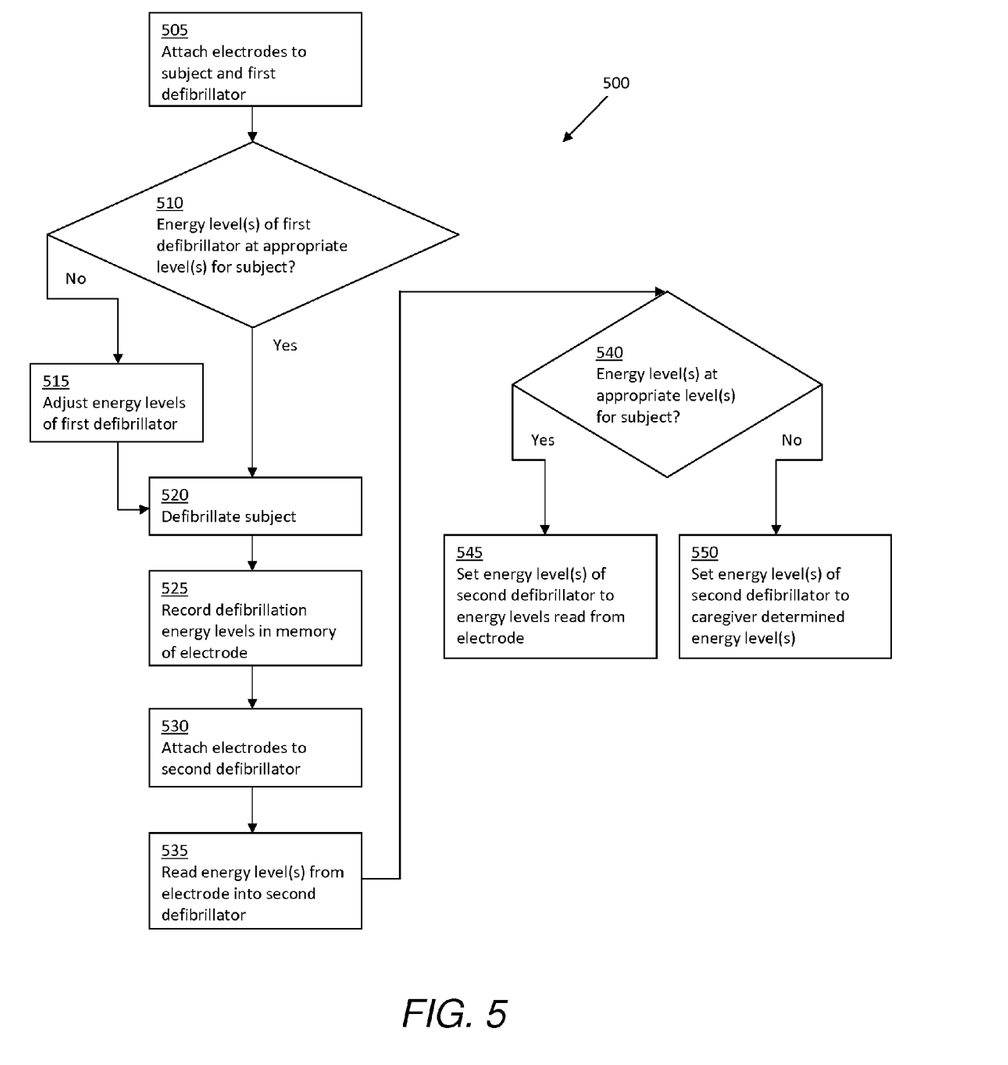
FIG. 5 is a flowchart of a method disclosed herein.

In an embodiment of a method for treatment of a subject experiencing cardiac distress, indicated generally at 500 in FIG. 5, a pair of electrodes may be attached to the subject and electrically coupled to a first defibrillator (act 505). A rescuer may determine if the defibrillator is set to deliver a defibrillation shock at an energy level appropriate for the subject (act 510). If the defibrillator is not set to deliver a defibrillation shock at an energy level appropriate for the subject, the rescuer may adjust the settings of the defibrillator such that it will deliver a defibrillation shock at an energy level appropriate for the subject (act 515). The subject may then be defibrillated with the defibrillator and attached electrodes (act 520). Circuitry in at least one of the electrodes may provide a signal to the defibrillator to query the defibrillator to obtain an indication of the energy level setting or settings of the defibrillator. The defibrillator may respond to the query from the electrode by sending a signal to the electrode with an indication of the energy level setting or settings of the defibrillator. This query operation may occur prior to or subsequent to the delivery of the defibrillation shock to the subject. The electrode which queried the defibrillator may store a representation of the indication of the energy level setting or settings of the defibrillator in a memory element of the electrode or in a memory element in a portion of an electrode pad in which the electrode is disposed (act 525). Alternatively, at least one of the electrodes may include circuitry configured to measure the energy level or levels of a defibrillation shock or shocks applied to the subject and to store a representation of the delivered energy level or levels in a memory element of the electrode or in a memory element in a portion of an electrode pad in which the electrode is disposed.

Subsequent to defibrillating the subject, the electrodes may be removed from the defibrillator while remaining attached to the subject, and subsequently electrically attached to a second defibrillator (act 530). The second defibrillator may be in a different location than where the subject was defibrillated with the first defibrillator. The second defibrillator may send a signal to the electrodes to query whether the electrodes include a memory element including information concerning a power level or levels of a defibrillation shock or shocks previously applied to the subject through the electrodes. An electrode including such a memory element may respond to the signal from the second defibrillator by sending a signal to the second defibrillator including an indication of the power level or levels of the defibrillation shock or shocks previously applied to the subject through the electrodes (act 535). The second defibrillator may adjust its power settings such that it would deliver a defibrillation shock or shocks to the subject having energy levels substantially similar to or the same as the energy level or levels of the defibrillation shock or shocks previously applied to the subject through the electrodes (act 545). The querying of the electrodes by the second defibrillator and/or the setting of the energy level or levels of the second defibrillator may occur automatically upon connection of the electrodes to the second defibrillator, responsive to a manual command by a caregiver, or automatically upon activation of the second defibrillator to deliver a defibrillation shock to the subject.

In some embodiments, the second defibrillator may provide a display of the energy level or levels read from the electrodes. A caregiver may accept these energy levels or override them and set the energy level or levels of the second defibrillator at different values (acts 540, 550).

In accordance with another aspect, an existing device such as an electrode, defibrillation electrode pad, or CPR assistance device may be modified to provide the functionality described herein. Circuitry associated with the device may be modified or augmented to query a defibrillator for a defibrillation energy setting and/or to measure the energy delivered during a defibrillation event. An existing memory element in the device may be utilized to store an indication of the defibrillation energy level and may be configured to provide an output indicative of the stored defibrillation energy level indication when queried by another device, for example a defibrillator. Such a modification may utilize existing circuitry in the device and thus may be performed at little or no cost.

Having thus described several aspects of at least one embodiment of this invention, it is to be appreciated various alterations, modifications, and improvements will readily occur to those skilled in the art. For example, it is to be appreciated that any of the features of any of the embodiments disclosed herein may be combined or substituted for features of any other embodiment disclosed herein. Acts of the method disclosed may be performed in alternate orders and one or more acts may be added to or omitted from the method or substituted by one or more alternative acts. Such alterations, modifications, and improvements are intended to be part of this disclosure, and are intended to be within the scope of the invention. Accordingly, the foregoing description and drawings are by way of example only.

What is claimed is:

1. A defibrillation electrode comprising:
   a non-volatile memory element; and
   at least one of a circuit and software configured to store, in the non-volatile memory element, at least one parameter associated with a use of the defibrillation electrode,
   wherein the defibrillation electrode is configured to be directly electrically connected with a first defibrillator such that the first defibrillator provides a signal indicative of the at least one parameter associated with the use of the defibrillation electrode to the non-volatile memory element; and
   wherein the defibrillation electrode is configured to be directly electrically connected with a second defibrillator to read the at least one parameter associated with the use of the defibrillation electrode.

2. The defibrillation electrode of claim 1, wherein the circuit is further configured to measure an energy level of a defibrillation shock delivered to a subject during application of the defibrillation shock to the subject.

3. The defibrillation electrode of claim 1, further comprising a marking providing an indication of the presence of the non-volatile memory element.

4. The defibrillation electrode of claim 1, wherein the at least one parameter associated with the use of the defibrillation electrode is an indication of whether the first defibrillator which applied the defibrillation shock through the electrode was set in a pediatric mode or in an adult mode.

5. The defibrillation electrode of claim 1, wherein the at least one parameter associated with the use of the defibrillation electrode is a signal indicative of an indication of an energy level delivered to a subject during the application of a defibrillation shock to the subject by the first defibrillator, and
   wherein the circuit is further configured to output a signal indicative of the energy level of the defibrillation shock delivered to the subject during the application of the defibrillation shock to the subject by the first defibrillator responsive to a query from the second defibrillator.

6. The defibrillation electrode of claim 1, further comprising an electrical connector configured to releasably electrically couple the defibrillation electrode to a defibrillator.

7. The defibrillation electrode of claim 1, wherein the at least one parameter associated with the use of the defibrillation electrode is at least one of identification information, model number, date of manufacture, expiration date, a history of treatment events provided to a subject through the defibrillation electrode, and an indication of an energy level delivered to the subject through the defibrillation electrode during the application of a defibrillation shock to the subject.

8. A defibrillation electrode pad comprising:
   a defibrillation electrode;
   a non-volatile memory element; and
   a circuit configured to store, in the non-volatile memory element, at least one parameter associated with a use of the defibrillation electrode pad,
   wherein the defibrillation electrode pad is configured to be directly electrically connected with a first defibrillator such that the first defibrillator provides a signal indicative of the at least one parameter associated with the use of the defibrillation electrode pad to the non-volatile memory element; and
   wherein the defibrillation electrode pad is configured to be directly electrically connected with a second defibrillator to read the at least one parameter associated with the use of the defibrillation electrode pad.

9. The defibrillation electrode pad of claim 8, wherein the at least one parameter associated with the use of the defibrillation electrode pad is at least one of identification information, model number, date of manufacture, expiration date, a history of treatment events provided to a subject through the defibrillation electrode pad, and an indication of an energy level delivered to the subject through the defibrillation electrode pad during the application of a defibrillation shock to the subject.

10. A defibrillation system comprising:
    a defibrillation electrode including a non-volatile memory element and a circuit configured to store, in the non-volatile memory element, at least one parameter associated with a use of the defibrillation electrode;
    a first defibrillator configured to provide a signal to the non-volatile memory element of the defibrillation electrode when the defibrillation electrode is directly electrically connected to the first defibrillator, the signal being indicative of the at least one parameter associated with the use of the defibrillation electrode; and
    a second defibrillator configured to be directly electrically connected to the defibrillation electrode to read the at least one parameter associated with the use of the defibrillation electrode.

11. The defibrillation system of claim 10, wherein a defibrillation energy level delivered by the first defibrillator is adjustable.

12. The defibrillation system of claim 11, wherein a defibrillation energy delivered by the first defibrillator is selectable between a pediatric energy level and an adult energy level.

13. The defibrillation system of claim 10, wherein the defibrillation electrode includes an electrical connector configured to releasably electrically couple the defibrillation electrode to the defibrillator.

14. The defibrillation system of claim 13, wherein the second defibrillator is configured to electrically couple to the electrode through the electrical connector.

15. The defibrillation system of claim 10, wherein the second defibrillator is configured to automatically read the at least one parameter associated with the use of the defibrillation electrode from the non-volatile memory element.

16. The defibrillation system of claim 10, wherein the second defibrillator is configured to read the at least one parameter associated with the use of the defibrillation electrode from the non-volatile memory element responsive to a command from a user.

17. The defibrillation system of claim 10, wherein the at least one parameter associated with the use of the defibrillation electrode is a signal indicative of an indication of a level of energy delivered to a subject during the application of a defibrillation shock to the subject by the first defibrillator, and wherein the second defibrillator is configured to set a defibrillation energy level to a level consistent with an energy level determined from the indication of the level of energy delivered to the subject read from the non-volatile memory element.

18. The defibrillation system of claim 17, wherein the second defibrillator is configured to display the set defibrillation energy level.

19. The defibrillation system of claim 17, wherein the second defibrillator includes an override configured to provide for an adjustment of the set defibrillation energy level.

20. The defibrillation system of claim 10, wherein the at least one parameter associated with the use of the defibrillation electrode is at least one of identification information, model number, date of manufacture, expiration date, a history of treatment events provided to a subject through the defibrillation electrode, and an indication of an energy level delivered to the subject through the defibrillation electrode during the application of a defibrillation shock to the subject.

21. A method for treatment of a subject experiencing cardiac distress, the method comprising:

attaching a pair of electrodes to the subject;

electrically coupling the pair of electrodes to a first defibrillator;

defibrillating the subject with the first defibrillator;

recording at least one parameter associated with a use of the pair of electrodes with the first defibrillator in a non-volatile memory element included in one of the pair of electrodes;

decoupling the pair of electrodes from the first defibrillator;

electrically coupling the pair of electrodes to a second defibrillator; and reading the at least one parameter associated with the use of the pair of electrodes with the first defibrillator from the non-volatile memory element into the second defibrillator.

22. The method of claim 21, further comprising:

determining a defibrillation energy setting of the first defibrillator;

determining if the defibrillation energy setting of the first defibrillator is appropriate for the subject based on the at least one parameter associated with the use of the pair of electrodes; and adjusting the defibrillation energy setting of the first defibrillator responsive to a determination that the defibrillation energy setting of the first defibrillator is not appropriate for the subject.

23. The method of claim 21, wherein the at least one parameter associated with the use of the pair of electrodes with the first defibrillator is an indication of a defibrillation energy setting of the first defibrillator and the method further comprises:

setting a defibrillation energy level of the second defibrillator to a level selected based on the indication of the defibrillation energy setting of the first defibrillator; and displaying the defibrillation energy level selected by the second defibrillator in a display of the second defibrillator.

24. The method of claim 23, further comprising:

determining if the defibrillation energy level selected by the second defibrillator is appropriate for the subject; and adjusting a defibrillation energy setting of the second defibrillator responsive to a determination that the defibrillation energy setting of the second defibrillator is not appropriate for the subject.

25. The method of claim 21, wherein the at least one parameter associated with the use of the pair of electrodes with the first defibrillator is at least one of identification information, model number, date of manufacture, expiration date, a history of treatment events provided to a subject through the pair of electrodes, and an indication of an energy level delivered to the subject through the pair of electrodes during the application of a defibrillation shock to the subject.

* * * * *